United States Patent [19]

Zaiger et al.

[11] Patent Number: Plant 6,078

[45] Date of Patent: Jan. 5, 1988

[54] NECTARINE TREE (JUNE BRITE)

[76] Inventors: Chris F. Zaiger, 537 Rosemore Ave.; Gary N. Zaiger, 1907 Elm Ave.; Leith M. Gardner, 1207 Grimes Ave.; Grant G. Zaiger, 2121 Elm Ave., all of Modesto, Calif. 95351

[21] Appl. No.: 671,904

[22] Filed: Nov. 16, 1984

[51] Int. Cl.[4] ..... A01H 5/03

[52] U.S. Cl. ..... Plt./41

[58] Field of Search ..... Plt./41

*Primary Examiner*—Robert E. Bagwill

[57] ABSTRACT

A new and distinct variety of nectarine tree whcih is of large size, medium dense, vigorous and upright growth; the tree being a productive and regular bearer of large, early ripening, firm, yellow flesh clingstone fruit with an attractive red skin color and having good eating, shipping and storage quality.

1 Drawing Figure

ORIGIN OF THE VARIETY

The present variety of nectarine tree was originated by us in the experimental orchard located near Modesto, Calif. The new nectarine tree was a selection from a large number of second generation seedlings which originated from a cross between Early Sun Grand Nectarine (U.S. Plant Pat. No. 1,420) and Zee Gold Nectarine (U.S. Plant No. 3,078). These seedlings which were grown and maintained under close observation by us gave many and varying characteristics, the present variety which evidenced distinctive desirable characteristics was selected for asexual reproduction and ultimate introduction into the trade to meet an existing demand for a nectarine so characterized.

SUMMARY OF THE VARIETY

The new and distinct variety of nectarine tree which is of large size, medium dense, vigorous and upright in growth and being a regular and productive bearer of large, yellow flesh, clingstone fruit characterized as to novelty by early ripening; the ripening period being 2 to 3 days earlier than Zee Gold Nectarine (U.S. Plant Pat. No. 3,087). The fruit is further characterized by having yellow skin color substantially overspread with red, firm flesh, good eating, shipping and handling qualities.

DESCRIPTION OF THE PHOTOGRAPHS

The accompanying photographs show typical specimens of the fruit and foliage of our new nectarine variety, with the upper and lower surfaces of the foliage being illustrated and typical specimens of the fruit, one of the said first specimens being depicted in cross section with stone remaining in place. The colors are as nearly true as reasonably possible in color representations of this type.

DESCRIPTION OF THE VARIETY

The following is a botanical description of our new nectarine tree, its foliage and fruit, as based on observations of specimens grown at Modesto, Calif., with color terminology (except those in common color terms) in accordance with Reinhold Color Atlas by A. Kornerup and J. H. Wansher.

Tree:
- *Size.*—Large.
- *Vigor.*—Vigorous.

- *Form.*—Upright.
- *Density.*—Medium dense.
- *Productivity.*—Productive.
- *Bearer.*—Regular.

Trunk:
- *Size.*—Stocky.
- *Surface.*—Shaggy.
- *Color.*—Brownish gray.

Branches:
- *Size.*—Medium stocky.
- *Texture.*—Smooth to medium rough.
- *Color.*—Brown to grayish brown.
- *Lenticels.*—Medium size. Medium number.

Leaves:
- *Size.*—Large. Average length — 6½" to 7½". Average width — 1½" to 1¾".
- *Texture.*—Smooth.
- *Form.*—Lanceolate. Acutely pointed.
- *Margin.*—Crenate.
- *Glands.*—Number 2 to 4. Usually 2. Located on base of leaf and upper portion of petiole. Reniform.
- *Petiole.*—Average length — ½". Average width — 1/16".
- *Color.*—Upper surface — deep green to dark green (28-E-8) to (28-F-7). Lower surface — grayish green (28-D-5) to (28-E-6).

Flower buds:
- *Size.*—Medium to large.
- *Length.*—Medium.
- *Form.*—Plump.

Flowers:
- *Size.*—Large — showy.
- *Color.*—Pink.
- *Pollen.*—Present.
- *Blooming period.*—Feb. 27, 1982 to Mar. 7, 1982. Varies slightly with climatic conditions.

Fruit:
- *Maturity when described.*—Firm ripe.
- *Date of first picking.*—June 1, 1982.
- *Date of last picking.*—June 6, 1982.
- *Size.*—Large — uniform. Average diameter axially — 2½" to 3". Average transversely in suture plane — 2½" to 2⅞".
- *Form.*—Nearly globose — slightly elongated in axial plane.
- *Suture.*—Extends from base to apex.

*Ventral surface.*—Rounded, lips vary from equal to unequal.

*Cavity.*—Rounded; circular. Average depth — ½". Average breadth — ¾".

*Base.*—Retuse.

*Apex.*—Rounded. Varies from slight depression to slight point.

Skin:

*Thickness.*—Medium.

*Texture.*—Medium — tenacious to flesh.

*Tendency to crack.*—None.

*Down.*—Wanting.

*Color.*—Yellow ground color (4-A-7) to (4-A-8). Almost entirely overspread with red (9-B-8) to (10-B-8).

Flesh:

*Juice.*—Moderate.

*Texture.*—Firm — meaty.

*Amygdalin.*—Wanting.

*Ripens.*—Comparatively even.

*Flavor.*—Mild.

*Aroma.*—Very little.

*Eating quality.*—Good.

*Color.*—Yellow (4-A-8) to cadmium orange (5-A-8). Stone cavity browish orange (7-B-8) to yellowish red (8-B-8).

Stone:

*Type.*—Clingstone.

*Size.*—Large. Average length — 1 7/16". Average breadth — 1⅛". Average thickness — ¾".

*Form.*—Ovid.

*Base.*—Straight to slight oblique.

*Apex.*—Acuminate.

*Sides.*—Equal to unequal Some with extended wings.

*Surface.*—Irregularly furrowed toward apex, pitted toward base.

*Ridges.*—Rounded toward apex.

*Tendency to split.*—Very slight.

*Color.*—Light brown to reddish brown (8-D-6) to (8-D-8).

Use: Dessert. Local and long distance shipping.

Keeping quality: Good.

Shipping quality: Good.

The nectarine tree and its fruit herein described may vary in slight detail due to soil, climatic conditions and cultural practices under which the variety may be grown. The description is that of the variety produced under ecological conditions prevailing at Modesto, Calif.

The following is claimed:

1. A new and distinct variety of nectarine tree, of large size, vigorous, upright growth and being a regular and productive bearer of large, early ripening, yellow flesh, clingstone fruit, ripening approximately 2 to 3 days before Zee Gold Nectarine (U.S. Plant Pat. No. 3,087); the fruit is further characterized by its uniform size, and attractive red skin color, its good eating, storage and shipping qualities.

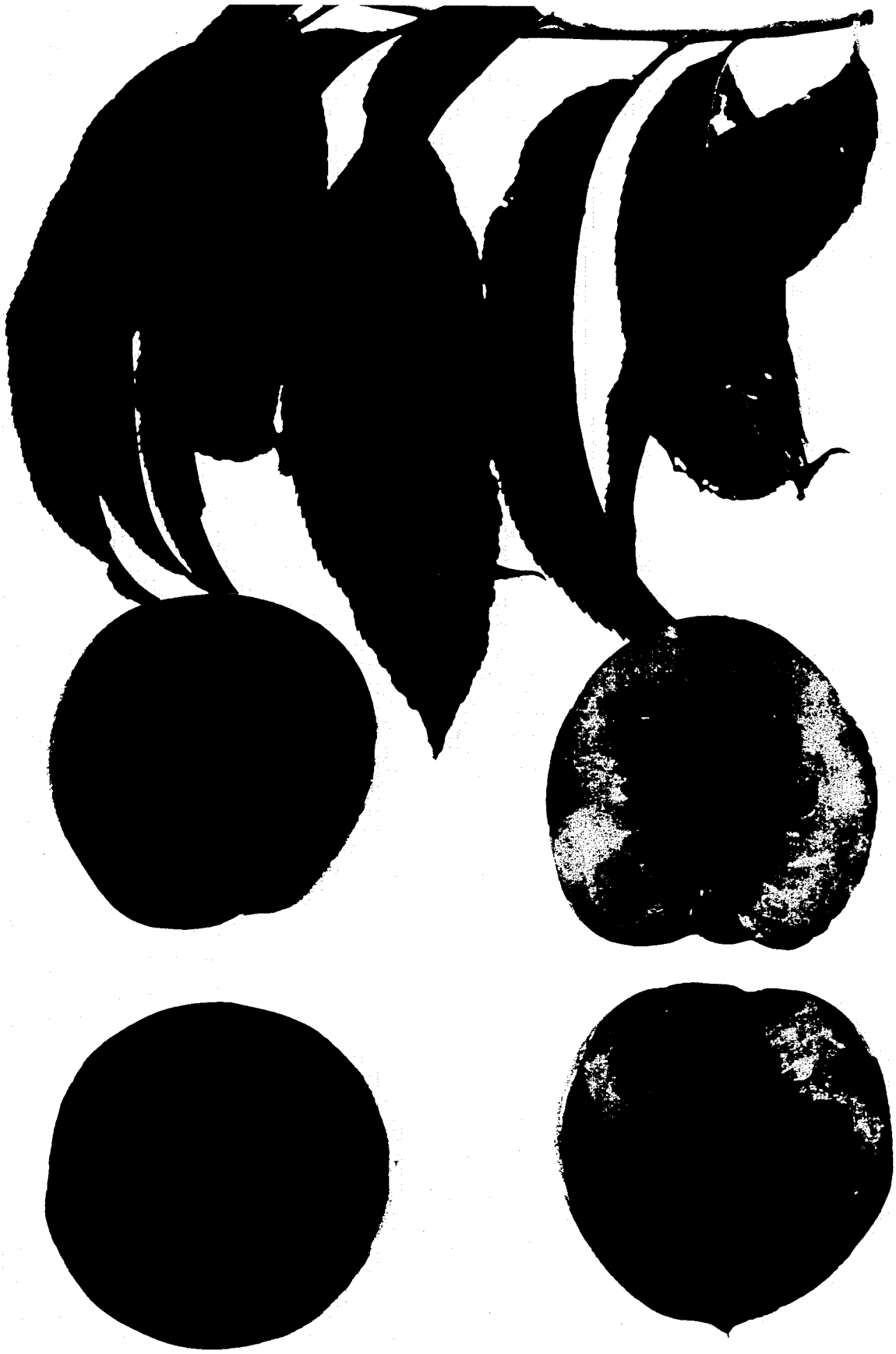

* * * * *